Feb. 6, 1973
A. MATON ET AL
Plant Pat. 3,300
CHRYSANTHEMUM PLANT
Filed June 23, 1971
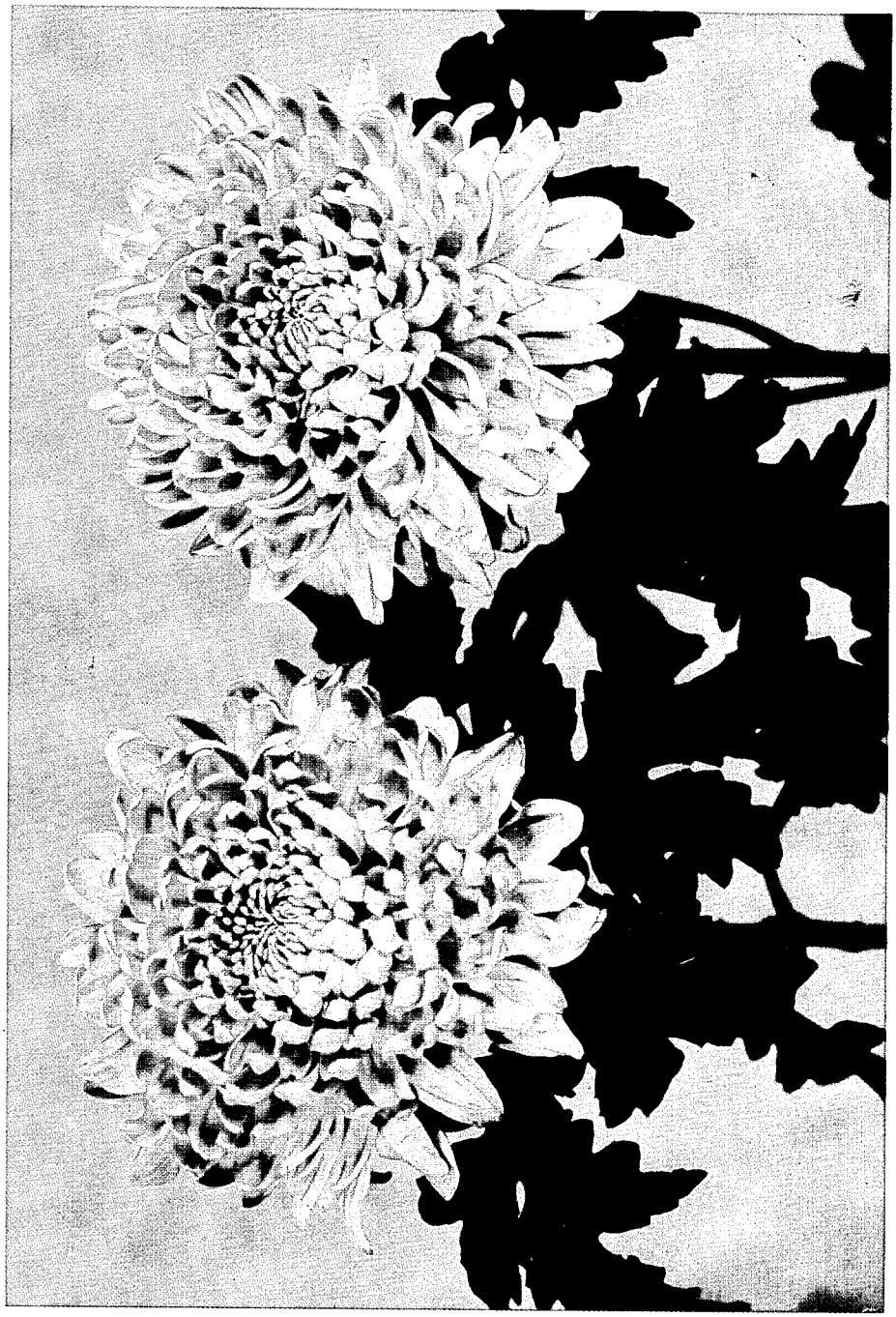

United States Patent Office

Plant Pat. 3,300
Patented Feb. 6, 1973

3,300

CHRYSANTHEMUM PLANT

Arthur Maton, Pana, Ill., and Walter H. Jessel, Jr., Doylestown, and William E. Duffett, Akron, Ohio, assignors to Webb Greenhouses, Inc., Pana, Ill.

Filed June 23, 1971, Ser. No. 156,140
Int. Cl. A01h *5/00*
U.S. Cl. Plt.—81 1 Claim

The present invention comprises a new and distinct cultivar of chrysanthemum plant which is a sport of the well-known, unpatented cultivar known in the United States as Pink Champagne.

The new cultivar is similar in many respects to Pink Champagne, having the same characteristics of:

(1) Plant habit.
(2) Flowering response.
(3) Flower form.
(4) Flowering period.

The new cultivar is distinguished from Pink Champagne by the following characteristics when grown under comparable conditions:

(1) Flowers approximately ½" smaller.
(2) A darker lavender flower color.
(3) Approximately 20% more petals.
(4) A more solid flower.
(5) Flowers reflex less at maturity.
(6) 2–3 days later response.

The new cultivar was discovered in a greenhouse in Pana, Ill., and when asexually reproduced by cuttings at Barberton, Ohio, was found to retain its distinctive characteristics through successive propagations.

The new cultivar when grown in the vicinity of Barberton, Ohio, has a response period of approximately 11 weeks, and the following detailed description is based on observations made of the new cultivar in a greenhouse in Barberton, Ohio. The response time, blooming period, color and total vigor may vary significantly with varying environmental conditions such as temperature, day length, and light intensity. Suggested flowering in the northern and western United States is from November thru April; coastal California, November thru April.

The accompanying drawing shows the unique characteristics of the new cultivar, the color being as nearly true as possible with color illustrations of this type. In the drawing, the new cultivar appears on the left and the comparison cultivar Pink Champagne on the right.

In the description which follows, color references are made to the Munsel Color Book, 1963 edition, and comparisons are made with the cultivar Pink Champagne. Where only a single value or description appears for the new cultivar, the same value or description applies also to the parent cultivar.

Botanical classification: *Chrysanthemum morifolium*

| | Deep Champagne | Pink Champagne |
|---|---|---|
| Bloom: | | |
| Size | 4¾" | 5¼". |
| Fully expanded | 5¼" | 5¾". |
| Borne | Singly on disbudded plants | |
| Stems | Strong | |
| Form | Semi-incurve | |
| Permanence | 10–14 days | |
| Color: | | |
| Center of flower | Dark lavender, 10P6/10. | Lavender, 10P6/6. |
| Base of petals | do | Do. |
| Inside of petals | Dark lavender, 10P6/10–10P6/8. | Lavender, 10P6/6–10P7/6. |
| Reverse of petals | Light lavender, 10P8/4. | Light lavender, 10P9/2. |
| Tonality from a distance. | Dark lavender | Lavender. |
| Discoloration | Lavender, 10P6/8 | Lavender, 10P7/6. |
| Petals: | | |
| Texture | Smooth | |
| Appearance and form | Tubular to open at base, broad deep keel, tapering to a hooded point | |
| Arrangement | Composite, whorled on a single receptacle | |
| Persistence | Resist shatter | |
| Fragrance | Typical chrysanthemum | |
| Reproductive organs: | | |
| Stamen | 0–15 | |
| Anthers | 0–15 | |
| Pollen | None—scant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 40" when grown with 15–16 week crop time, with 5–6 long day weeks | |
| Spread | None—grown, singlestem | |
| Foliage: | | |
| Top side | Green, 7.5GY3/4 | |
| Size | 6" long, 3¼" wide | |
| Quantity | Numerous | |
| Shape | Spatulate lobed | |
| Texture | Smooth | |
| Ribs and veins | Prominent | |
| Edge | Deeply indented | |
| Serration | Very coarse | |
| Under side | Light gray, 7.5GY5/4 | |
| Stipules | Prominent | |

We claim:

1. A new and distinct cultivar of chrysanthemum characterized particularly as to its uniqueness when compared to the parent cultivar Pink Champagne by its darker lavender flower color, approximately 20% more petals, more solid flower, flowers which reflex less at maturity, and its 2–3 days later response.

No references cited.

ROBERT E. BAGWILL, Primary Examiner

UNITED STATES PATENT OFFICE
CERTIFICATE OF CORRECTION

Patent No. PP-3,300 Dated February 6, 1973

Inventor(s) Arthur Maton, Walter H. Jessel, Jr. and William E. Duffett

It is certified that error appears in the above-identified patent and that said Letters Patent are hereby corrected as shown below:

In column 2, line 4, opposite "Size" and under "Deep Champagne", the description should read --4-3/4--.

In column 2, line 31, opposite "Spread", change "singlestem" to --single stem--.

Signed and sealed this 1st day of October 1974.

(SEAL)
Attest:

McCOY M. GIBSON JR.
Attesting Officer

C. MARSHALL DANN
Commissioner of Patents

USCOMM-DC 60376-P69
* U.S. GOVERNMENT PRINTING OFFICE : 1969 O—366-334